United States Patent [19]

Eisenberg et al.

[11] 4,116,227
[45] Sep. 26, 1978

[54] COMBINATION CATHETER VENTING AND URINE SAMPLE COLLECTING UNIT AND METHOD OF MAKING THE SAME

[75] Inventors: Melvin I. Eisenberg, Chicago; Norman Levy, Highland Park; Glenn L. Beall, Gurnee, all of Ill.

[73] Assignee: Plasco, Inc., Gurnee, Ill.

[21] Appl. No.: 700,729

[22] Filed: Jun. 28, 1976

[51] Int. Cl.² .................. A61B 10/00; A61M 25/00
[52] U.S. Cl. ................................ 128/2 F; 128/275; 128/295; 128/349 R
[58] Field of Search ......... 128/2 F, 275, 295, 349 R; 210/436, DIG. 23

[56] References Cited
U.S. PATENT DOCUMENTS

| 2,832,338 | 4/1958 | Ryan | 128/214 R |
|---|---|---|---|
| 3,543,743 | 12/1970 | Foderick | 128/2 F |
| 3,690,315 | 9/1972 | Chittenden et al. | 128/275 |
| 3,851,650 | 12/1974 | Darling | 128/275 |
| 3,906,935 | 9/1975 | Raia et al. | 128/2 F |
| 3,906,958 | 9/1975 | Knox | 128/349 R |
| 4,013,064 | 3/1977 | Patel et al. | 128/2 F |

Primary Examiner—Dalton L. Truluck

Attorney, Agent, or Firm—Wallenstein, Spangenberg, Hattis & Strampel

[57] ABSTRACT

A combination catheter venting and urine sample collecting unit comprises a hollow open-ended body having an outlet and adapted to receive and communicate with a conduit extending to a urine collecting reservoir and an inlet adapted to receive and communicate with a catheter extending to the bladder. The body further has a urine collection needle-receiving port and a number of circumferentially spaced venting apertures spaced longitudinally of the said needle-receiving port. A strip of bacteria and liquid impermeable, and air-permeable filtering material is positioned in liquid-sealing relation beneath the venting apertures. The filtering material is carried on the outside of an open-ended support tube having circumferentially spaced apertures in alignment with said venting apertures. The support tube is enveloped by said body which is preferably molded about the tube. The body has a continuous outer annular indented wall surface upon which the needle-receiving port opens. A self-sealing band of rubber-like material is stretched and supported on the indented wall surface to making a liquid and air sealing relationship with the defining walls of the needle-receiving port.

7 Claims, 6 Drawing Figures

COMBINATION CATHETER VENTING AND URINE SAMPLE COLLECTING UNIT AND METHOD OF MAKING THE SAME

BACKGROUND OF THE INVENTION

This invention relates to devices for venting urine drainage systems and collecting mid-stream urine samples in such systems.

Urine drainage systems are utilized when patients do not have any control over their urination, making it necessary for an uretheral catheter to be extended into the patient's bladder. The outlet end of the catheter is then directly or indirectly connected to a suitable urine collection reservoir, such as a flexible bag or the like, into which the urine drains by gravity. Even when the patient is not urinating, a column of previously collected urine can build up within the urine drainage system, which column of urine creates a suction at the inlet end of the catheter which can cause the bladder to prolapse around the catheter tip. This suction draws the bladder into the catheter inlet openings and can cause lesions to develop in the bladder mucosa. To eliminate this suction condition, vents are provided either directly in the catheter, as disclosed in U.S. Pat. No. 3,429,314, granted Feb. 25, 1969, or vents are provided in an adapter unit interconnected between the outlet end of the catheter and the urine collection reservoir or conduit leading thereto. Such an adapter is disclosed in U.S. Pat. No. 3,820,546, granted June 28, 1974. To prevent the ingress of bacteria into the urine drainage system, a bacteria filtering material is positioned over the vent-forming apertures involved in a manner which makes a liquid-tight seal with the defining walls thereof, thereby permitting the passage of air into the urine drainage system, but preventing the passage of urine from, and bacteria with the air into, the urine drainage system.

It is frequently necessary to collect specimens of the uring flowing into the urine collection reservoir bag which is provided at the bottom thereof with a closeable drainage tube which is used to drain the urine collection bag. The obtainment of urine specimens for test purposes from this drainage tube is unsatisfactory except where the specimen is immediately collected as it enters the bag. However, when the urine drainage bag accumulates a body of urine draining therein over a period of time, the urine then collected represents urine specimens draining into the bag over a period of time. In order to collect the urine midstream without contamination by urine flow at different times, it has been found desirable to provide a means for collecting urine during its passage through the catheter into the urine drainage bag. Accordingly, a urine collection adapter unit is sometimes provided which is connected between the catheter extending to the bladder and the urine collection reservoir or conduit extending thereto, the adapter unit having a specimen collection port over which is secured a layer of natural rubber latex or the like which can be punctured by a needle but which forms an immediate seal upon withdrawal of the needle therefrom. A similar speciment collecting adapter is shown in U.S. Pat. No. 2,832,838, granted Apr. 29, 1958.

It is an object of the present invention to provide an improved catheter venting adapter unit which is designed so that it can be made on a mass-production basis at a minimum cost. A related object of the invention is to provide a method for making such a venting adapter unit.

Another object of the invention is to provide a mid-stream urine collection adapter unit which is designed to be mass-produced at a minimum cost.

Still another object of the present invention is to provice improved catheter venting and mid-stream urine collection devices which can be manufactured at a minimum cost and overall size and complexity.

SUMMARY OF THE INVENTION

Thus, in accordance with one of the features of the present invention, a catheter venting adapter unit is provided with a unique construction where it can be fabricated more easily and inexpensively than similarly functioning adapter units of the prior art. Like these prior adapter units it includes a body made of a molded synthetic plastic material having a passageway extending longitudinally therethrough from its inlet end to its outlet end thereof. Also, the adapter unit body preferably has a plurality radially outwardly extending circumferentially spaced venting apertures in communication between the longitudinal passageway of the adapter unit body and the exterior thereof. In accordance with the present invention, the aforementioned bacteria and liquid impermeable filter is formed by a strip of such filter material carried on an apertured support tube which, together with the strip of filter material, is enveloped by the adapter unit body so that the filter material is sandwiched between the support tube and the synthetic plastic material of the adapter unit body.

The adapter unit construction described lends itself to a very simple and economical fabrication process, wherein the filter support tube is initially carried on a mandrel supported on the lower half of an injection mold assembly, the mandrel forming the longitudinal passageway of the completed adapter body. A strip of the filter material longer than the circumference of the support tube is placed around the support tube and sealed tightly thereto, leaving one or more tabs extending therefrom. The tabs are sandwiched between the upper and lower mold parts to hold the filter medium in a stationary position upon the support tube during the flow of synthetic plastic material through the mold. When the plastic material in the mold hardens, the mold parts are separated and the mandrel pulled from the support tube and molded adapter unit body, to separate the completely molded product from its mold-forming environment.

In accordance with another aspect of the present invention, a mid-stream urine collection adapter unit is provided which includes a body preferably made of synthetic plastic material and having an outer annular recess portion into which opens a urine collection port. A latex rubber band sized to be supported in the recess of the adapter unit body in a stretched condition is simply pushed along the adapter body into a position within the recess of the adapter unit body where it covers the urine collection port.

In accordance with the most preferred form of the invention, both the aforesaid catheter venting adapter unit and the mid-stream urine specimen collection adapter unit are integrated into a single molded synthetic plastic body, with the venting apertures and the urine collection port most advantatiously in longitudinally spaced positions on the body.

The above and other features of the invention and the advantages thereof will become more apparent upon making reference to the specification to follow, the claims, and the drawings.

DESCRIPTION OF PREFERRED EMBODIMENT OF THE INVENTION

Figure 1:
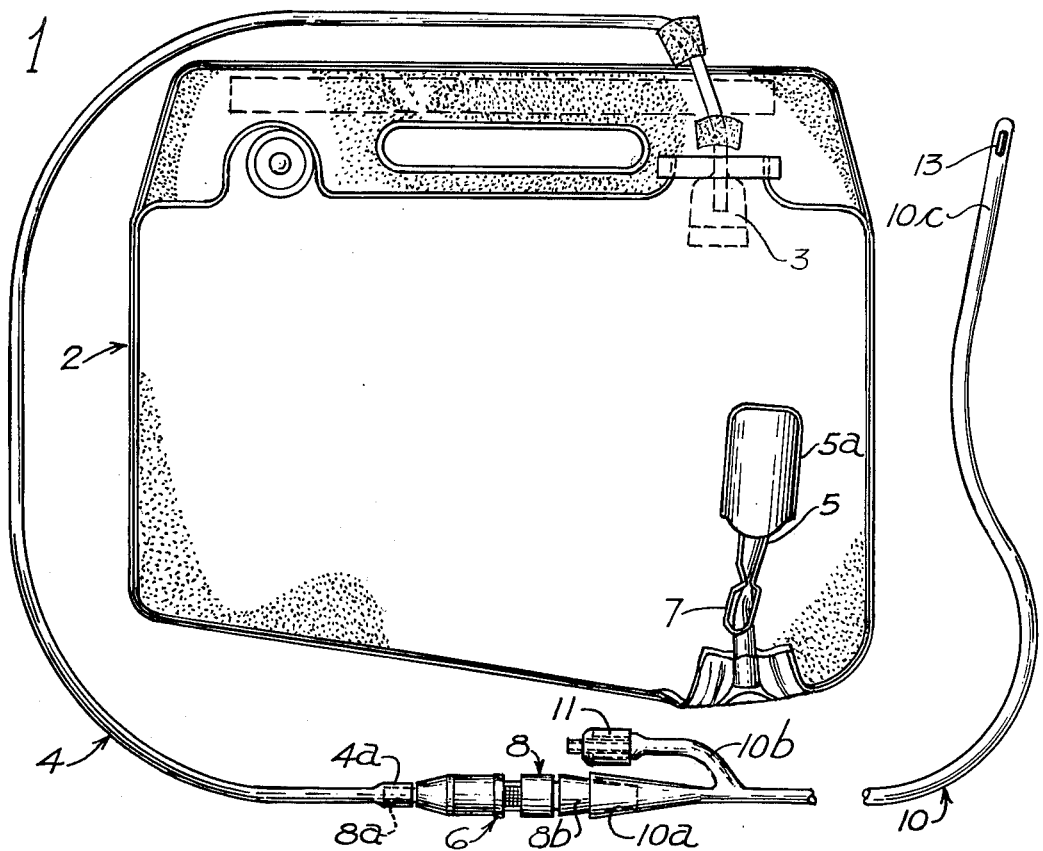
FIG. 1 is an elevational view of a urinary drainage bag with the combination catheter vent and urine sample collection unit of the invention interconnected between a bag inlet tube and a catheter to be extended through the urethral canal to a patient's bladder.

Refer now to FIG. 1 which shows the application of the present invention to a urine drainage system including a urine drainage bag 2 into the upper portion of which is connected the bottom portion of a tube 4 extending into communication with a valve 3 similar to that disclosed in U.S. Pat. No. 3,473,532, granted Oct. 21, 1969, to M. I. Eisenberg. The drainage bag 2 has extending from the bottom thereof a drain tube 5 which is bent upwardly and inserted into a downwardly opening pocket 5a. A pinch-clamp 7 seals off the tube 5 to prevent leakage of urine from the bag 2.

The inlet end of the tube 4 is frictionally fitted over the cylindrical outlet end 8a of a combination catheter vent and urine sample collection adapter unit 6 of the present invention. A Foley catheter 10 is shown with its enlarged outlet end 10a stretched over the outwardly tapering inlet end 8b of the adapter unit 6. The Foley catheter 10 has a water inlet arm 10b with a suitable one-way valve 11 adapted to receive a syringe for filling a closed-ended peripheral passageway (not shown) in the catheter 10 with liquid in the well known manner, to expand or balloon the inlet end 10c of the catheter 10 at a point inwardly of urine-inlet ports 13 in the catheter which face laterally outwardly. The Foley catheter 10 has, in addition to the peripheral passageway communicating with the arm 10b, a central longitudinal passageway (not shown) which communicates with the urine collection ports 13. The ballooning of the catheter 10 at the inlet end 10c thereof is for the purpose of retaining the inlet end of the catheter in place within the patient's bladder when the catheter has been inserted through the uretheral canal into the bladder.

As previously indicated, to eliminate any suction within the catheter 10 which might tend to draw the bladder tightly around and into the catheter 10, it is desirable to provide a liquid and bacteria-sealed vent somewhere along the urine drainage system to equilize the pressure inside and outside of the catheter. This vent is provided by the adapter 6 now to be described. Also, the adapter unit 6 provides a port which is normally sealed from the exterior of the unit 6, for collecting samples of urine as it passes through the catheter 10, adapter unit 6 and drainage tube 4 into the drainage bag 2, before such urine has been contaminated or mixed with urine which has previously drained into the bag 2.

Figure 2:
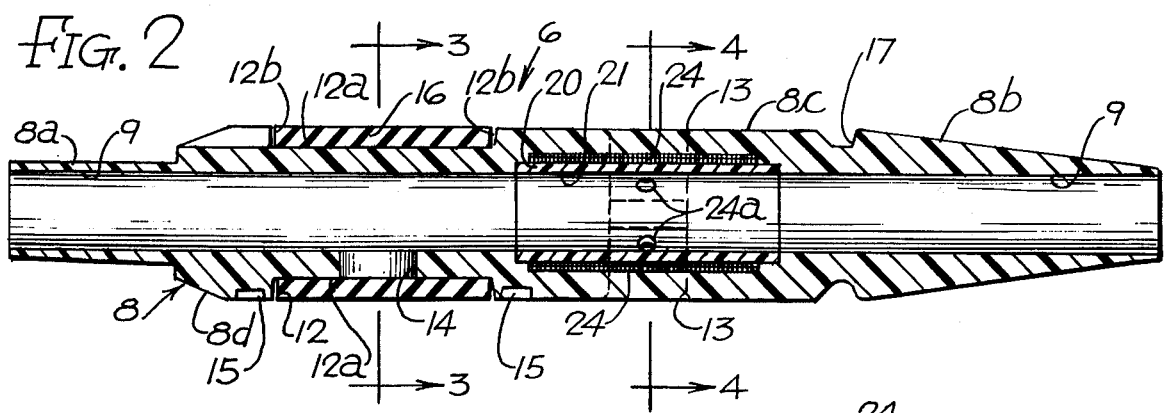
FIG. 2 is a greatly enlarged, longitudinal sectional view through the combination catheter vent and urine sample collection unit shown in FIG. 1.
Figure 3:
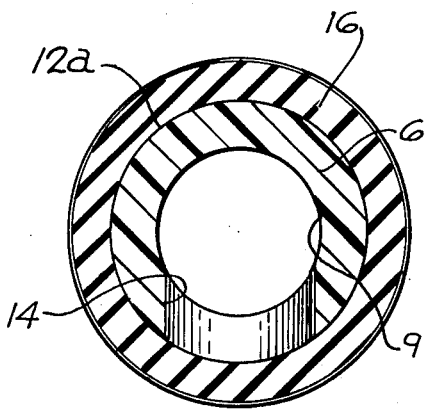
FIG. 3 is an enlarged transverse sectional view through the urine collection needle-receiving portion of the unit shown in FIG. 2, taken along section line 3—3 thereof.
Figure 4:
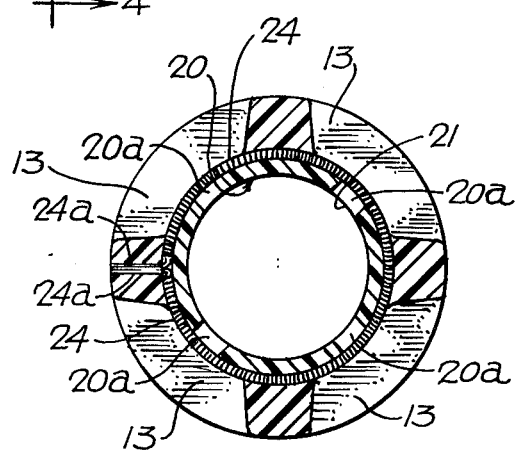
FIG. 4 is an enlarged transverse sectional view through the catheter venting apertures of the unit shown in FIG. 2, taken along section line 4—4 thereof.

Refer now more particularly to FIGS. 2 through 4 which shows the construction of the adapter unit 6. The adapter unit 6 has a main body 8 preferably made of a suitable molded synthetic plastic material as, for example, the synthetic plastic compositions identified as SAN (a styrene-acrylonitrile) and ABS (acrylonitrile butadiene styrene). A preferable SAN synthetic plastic material is sold by the Monsanto Company by the identification No. LNA 312060, Crystal No. 357. The adapter unit body 8 has a longitudinally extending passageway 9 opening onto the axially outwardly facing ends of the adapter unit body 8. The adapter unit body has a main cylindrical central portion 8c interrupted at one point by four, circumferentially spaced, radially outwardly opening, venting apertures 13 and at another point spaced axially from the venting apertures 13 by an annular indented portion 12 defined by a recessed radially outwardly facing surface 12a terminating in radially outwardly extending shoulders 12b—12b. A urine collection needle-receiving port 14 extending from the passageway 9 opens radially outwardly upon the recessed surface 12a. At the outer end of the adapter unit body 8 in the illustrated embodiment of the invention the cylindrical central portion thereof merges with an outwardly tapering portion 8d, in turn, merging with the reduced cylindrical outer end portion 8a thereof. Adjacent the inlet end of the adapter unit body 8 the cylindrical portion 8a terminates in an annular recess 17, in turn, merging with the previously described outwardly tapering inlet portion 8b of the adapter unit body 8.

The needle-receiving port 14 communicating with the longitudinal passageway 9 is sealed by a self-sealing band 16 made of a resilient natural rubber latex or the like which maintains an air and liquid-tight seal about the defining walls of the port 14 and is self-sealing when a needle pushed through the band to gain entry to passageway 9 is withdrawn therefrom. The natural rubber latex band 16 is preferably made of a partially transparent material so that the outlines of the port 14 can be viewed through the band. However, to ensure that the user can readily locate the port 14 through the band 16, the body portion 8 on opposite sides of the indented portion 12 of the adapter unit body 8 can be provided with arrow-shaped indentations 15—15 in alignment with the port 14 to identify the port's location. It should be appreciated that the provision of the indented portion 12 and the band 16 which can be readily expanded and pushed over the adapted unit body to drop within the recessed portion 12 provides a very easy to assemble combination of an adapter unit body with a sample port and a port sealing member 12.

The venting apertures 13 of the adapter unit body 8 are underlied by a body 24 of a bacteria and liquid impermeable and air-permeable filtering material, samples of which have been available on the open market for several years. For example, such filters are presently being sold under the trademark ACROPOR and manufactured by the Gelman Instrument Company of Ann Arbor, Mich. These filters come in thin sheet form and are flexible so that they an be readily bent around tubular shapes and the like. Thus, as shown best in FIGS. 2 and 4, a strip 24 of such filter material is tightly wound and secured around a filter support tube 20 where it overlies apertures 20a formed in the tube which are in alignment with the venting apertures 13 in the adapter unit body 8. The support tube 20 is preferably secured within the adapter unit body 8 when the body is molded around the support tube, in a manner to be described. As best shown in FIG. 2, the synthetic plastic material preferably forming the adapter unit body 8 envelopes the outer end portions of the support tube 20 as well as the portions of the strip 24 of filter material out of alignment with the venting apertures 13, so that the filter material is effectively sandwiched in liquid-tight relation between the adapter unit body 8 and the support tube 20. The support tube 20 has a longtudinally extending passageway 21 of about the same diameter as the passageway 9 in the adapter unit body 8 and is in alignment therewith so that urine readily passes through the tube 20. The use of the support tube 20 to hold the strip of filtering material 24 is primarily for the purpose of simplifying the method of fabrication of the combination catheter vent and urine sample collecting unit 6 now to be described.

Figure 5:
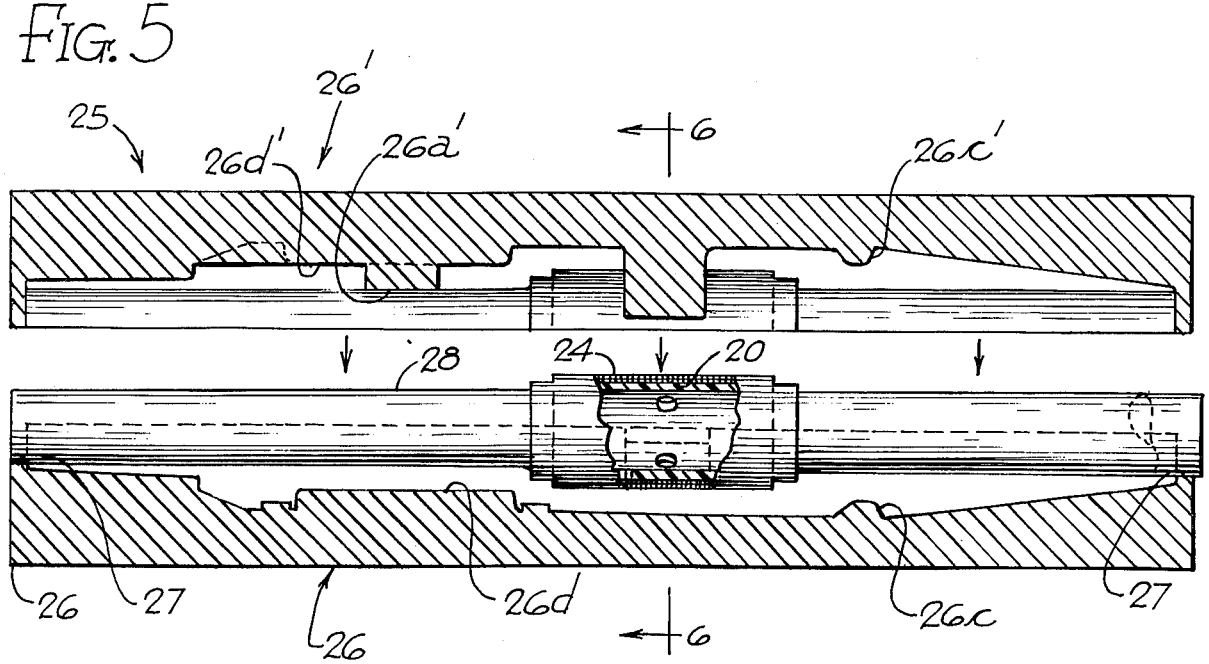
FIG. 5 is a view showing separated lower and upper mold parts for forming the combination catheter vent and urine sample collection unit shown in FIGS. 1 through 4, with a mandrel carrying a filter support tube with a filter strip secured thereto supported on the lower mold part.
Figure 6:
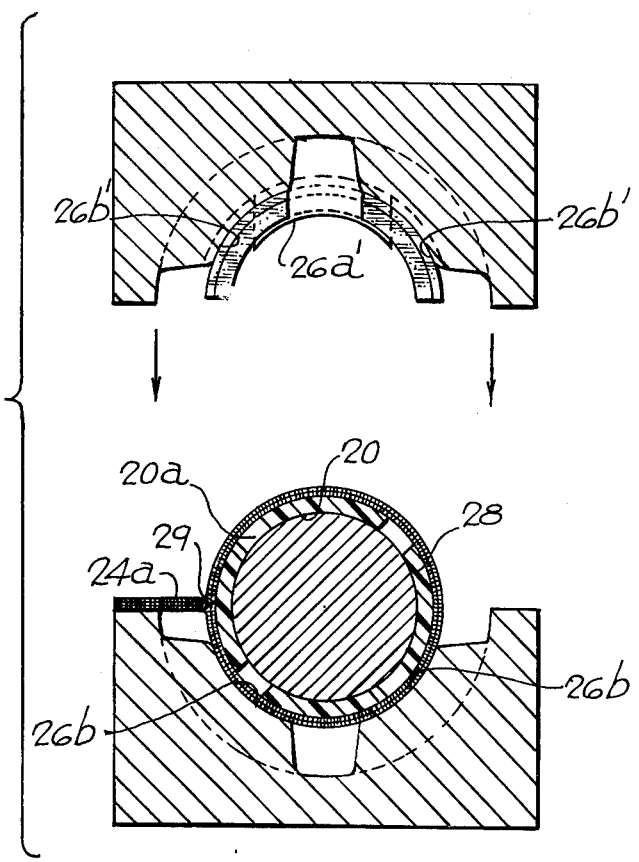
FIG. 6 is an enlarged transverse sectional view through the separated mold parts and mandrel shown in FIG. 5, taken along section line 6—6 thereof.

Reference should now be made to FIGS. 5 and 6 which illustrates this fabrication method. As there-shown, an injection mold 25 is formed from upper and lower mold-forming parts 26' and 26 which, when brought together around a longitudinally extending mandrel 28, define a continuous cavity defining the various inner and outer surfaces of the adapter unit body 8 previously described. The mandrel 28 is shown supported on support surfaces 27—27 of the lower mold part 26, the mandrel 28 carrying the support tube 20 with the strip of filter material 24 tightly secured therearound. In the most preferred form of the invention, the strip of filter material 24 is adhesively or otherwise sealed tightly around the tube at a securing point 29 short of the ends of the strip of material involved. The ends of the strip beyond the point 29 form tabs 24a extending radially outwardly along the upper surface of the lower mold part 26, as best shown in FIG. 6. The tabs 24a are sandwiched between the lower and upper mold parts when the upper mold part 26' is brought tightly down into engagement with the lower mold part 26. The tabs held in place between the upper and lower mold parts maintain the filter material in a fixed position on the tube 20, despite the flow of synthetic plastic material thereby before the plastic material has hardened.

The upper and lower mold parts are shown with various projecting portions 26a', 26b—26b and 26b'—26b', 26c-26c', and 26d-26d' which form the various aforementioned apertures and indentations on the outside of the adapter unit body 8. The aperture-forming projections 26b—26b and 26b'—26b' tightly press down against the strip of filter material 24 after the synthetic plastic material has hardened. The completed adapter unit 6 is removed from the mold simply by separating the upper and lower parts and then pulling the completed unit from the mandrel 28.

The present invention as described has thus provided an easy to fabricate combination catheter vent and urine sample collection unit and method of making the same.

It should be understood, that numerous modifications may be made in the most preferred form of the invention described without deviating from the broader aspects of the invention. For example, while the present invention has its most important application where the adapter unit body 8 has both the venting apertures 13 and the urine sample port 14, the features respectively associated with these ports and apertures can also be incorporated in adapter units which have only the sample port 14 or the venting apertures 13.

We claim:

1. A combination catheter vent and urine sample collecting unit to be connected between a catheter extending to the bladder and a conduit extending to a urine collecting reservoir, said unit comprising: a one piece body of molded synthetic plastic material having a straight passageway extending longitudinally therethrough from an inlet end to an outlet end of said body aligned therewith, said body at the outlet end being adapted to receive and communicate with said conduit extending to said urine collecting reservoir and at the inlet end thereof being adapted to receive and communicate with said catheter extending to said bladder, said body having a laterally opening and extending urine collection needle-receiving aperture between said longitudinal passageway and the exterior of said body and a number of laterally opening and extending and circumferentially spaced venting apertures spaced longitudinally of said urine collection needle-receiving aperture and in air communication between said longitudinal passageway and the exterior of said body, an open-ended support tube in said body having a longitudinal passageway forming a continuation of said body passageway and having circumferentially spaced laterally opening and extending apertures communicating with the support tube passageway and in alignment with said laterally opening and extending venting apertures of said body, said support tube having a longitudinal opening therethrough in communication and in alignment with said body passageway, a bacteria and liquid impermeable and an air-permeable strip of filtering material supported on the outside of said support tube where it extends over said apertures in said support tube and underlies said venting apertures in said body where it makes liquid-sealing relation to the defining walls of said venting apertures in said body, and a urine collection needle puncturable self-sealing layer of material on said body covering said urine collection needle-receiving aperture and making a liquid and air sealing relationship with the defining walls of the latter laterally opening and extending aperture.

2. The combination catheter vent and urine sample collection unit of claim 1 wherein said filtering material supported on said tube extends beyond the margins of said venting apertures in said body where said filtering material is sandwiched between portions of said body and the outer surface of said support tube.

3. The combination catheter vent and urine sample collecting unit of claim 1 wherein said body has a continuous outer annular indented wall surface portion extending around said body and upon which said needle-receiving aperture opens, and said self-sealing layer of material being a band of radially outwardly stressed resilient flexible rubber-like material in said indented outer surface portion of said body and resiliently hugging said indented wall surface to making a liquid and air sealing relationship with the defining walls of said needle-receiving aperture.

4. A catheter venting unit adapted to be connected between a catheter extending into the bladder and a conduit extending to urine collection reservoir, said catheter venting unit comprising a body made of synthetic plastic material and having a passageway extending longitudinally therethrough from an inlet end to an outlet end of said body, said body at the outlet end being adapted to receive and communicate with said conduit extending to said urine collecting reservoir and at the inlet end thereof being adapted to receive and communicate with said catheter extending to said bladder, said body having a radially outwardly extending and opening aperture in air communication between said longitudinal passageway and the exterior of said body, a bacteria and liquid impermeable and an air-permeable filtering material positioned in liquid-sealing relation to the defining walls of said venting aperture, a filter support tube in said body supporting on the outside thereof said filtering material which filtering material and support tube are closely enveloped by, and in contacting relationship over substantially all of the exposed radially outwardly facing surfaces thereof with synthetic plastic material forming said body, and said filter support tube having at least one radially outwardly extending and opening aperture in alignment with said venting aperture in said body and covered by said filtering material.

5. The catheter venting unit of claim 4 wherein said body has a number of said venting apertures circumferentially spaced apart in said body, said filter support tube having a number of radially outwardly extending and opening apertures in alignment with said venting apertures in said body, and said filtering material being a strip of such material enveloping said support tube and covering said apertures therein.

6. The catheter venting unit of claim 4 wherein said connector body is a one piece molded body which is molded around said support tube and directly merges with the outer end portions of said support tube.

7. The catheter venting unit of claim 4 wherein said filter support tube passageway forms a shoulderless continuation of the portion of said body passageway beyond the opposite ends of said support tube.

* * * * *